(12) United States Patent
Hasegawa

(10) Patent No.: US 11,863,374 B2
(45) Date of Patent: Jan. 2, 2024

(54) DISTRIBUTED CONTROL SYSTEM, AUTOMATIC ANALYSIS DEVICE, AND AUTOMATIC ANALYSIS SYSTEM

(71) Applicant: HITACHI HIGH-TECH CORPORATION, Tokyo (JP)

(72) Inventor: Takafumi Hasegawa, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 535 days.

(21) Appl. No.: 17/260,039

(22) PCT Filed: May 27, 2019

(86) PCT No.: PCT/JP2019/020808
§ 371 (c)(1),
(2) Date: Jan. 13, 2021

(87) PCT Pub. No.: WO2020/021839
PCT Pub. Date: Jan. 30, 2020

(65) Prior Publication Data
US 2022/0006691 A1 Jan. 6, 2022

(30) Foreign Application Priority Data
Jul. 26, 2018 (JP) .................................. 2018-140550

(51) Int. Cl.
*H04L 41/0686* (2022.01)
*H04L 43/0811* (2022.01)
(Continued)

(52) U.S. Cl.
CPC ... *H04L 41/0686* (2013.01); *G01N 35/00623* (2013.01); *G01N 35/00871* (2013.01);
(Continued)

(58) Field of Classification Search
CPC ............ H04L 41/0686; H04L 43/0811; G01N 35/00623; G01N 35/00871;
(Continued)

(56) References Cited

U.S. PATENT DOCUMENTS 8,565,238 B2* 10/2013 Saegusa .............. H04L 12/4035
370/254
2010/0105143 A1 4/2010 Kawamura
(Continued)

FOREIGN PATENT DOCUMENTS

JP 10-334035 A 12/1998
JP 2007-200212 A 8/2007
(Continued)

OTHER PUBLICATIONS

International Search Report, PCT/JP2019/020808, dated Aug. 27, 2019, 2 pgs.
(Continued)

*Primary Examiner* — Mohammad Ali
*Assistant Examiner* — Sheela Rao
(74) *Attorney, Agent, or Firm* — Volpe Koenig

(57) ABSTRACT

In a distributed control system, when the determination that an error has occurred is made as a result of comparison of correct connection information retained in a storage unit and connection information of an actually connected control object device or terminal communication device by a comparison unit, a central computation device outputs a display signal of an abnormal part to a display device, and the display device displays the abnormal part on the basis of the display signal. A distributed control system and an automatic analysis device provided with the same, and an automatic analysis system are thereby provided, whereby an erroneous connections or defects can be more easily and reliably (Continued)

detected than in the prior art, even when a plurality of control boards are distributedly arranged in the same device.

9 Claims, 6 Drawing Sheets

(51) Int. Cl.
    *G01N 35/00*     (2006.01)
    *G16H 10/40*     (2018.01)
    *G06F 11/30*     (2006.01)
    *G06F 11/32*     (2006.01)
    *G01R 31/317*     (2006.01)

(52) U.S. Cl.
    CPC .... *G01R 31/31722* (2013.01); *G06F 11/3055* (2013.01); *G06F 11/326* (2013.01); *G16H 10/40* (2018.01); *H04L 43/0811* (2013.01); *G01N 2035/0091* (2013.01); *G01N 2035/00326* (2013.01); *G01N 2035/00891* (2013.01)

(58) Field of Classification Search
    CPC .......... G01N 2035/00326; G01N 2035/00891; G01N 2035/0091; G01R 31/31722; G06F 11/3055; G06F 11/326; G16H 10/40
    See application file for complete search history.

(56) References Cited

U.S. PATENT DOCUMENTS

| | | |
|---|---|---|
| 2013/0159332 A1 | 6/2013 | Matsubayashi et al. |
| 2016/0006648 A1* | 1/2016 | Saegusa ............ H04L 12/40182 |
| | | 370/236 |

FOREIGN PATENT DOCUMENTS

| | | |
|---|---|---|
| JP | 2010-101719 A | 5/2010 |
| JP | 2541844 A1 | 1/2013 |
| JP | 2013-125428 A | 6/2013 |
| JP | 2014-044046 A | 3/2014 |
| JP | 2018-019199 A | 2/2018 |

OTHER PUBLICATIONS

International Preliminary Report on Patentability dated Dec. 2, 2020 for PCT International Application No. PCT/JP2019/020808.

Extended European Search Report dated Mar. 23, 2022 for European Patent Application No. 19842296.6.

\* cited by examiner

[FIG. 1]
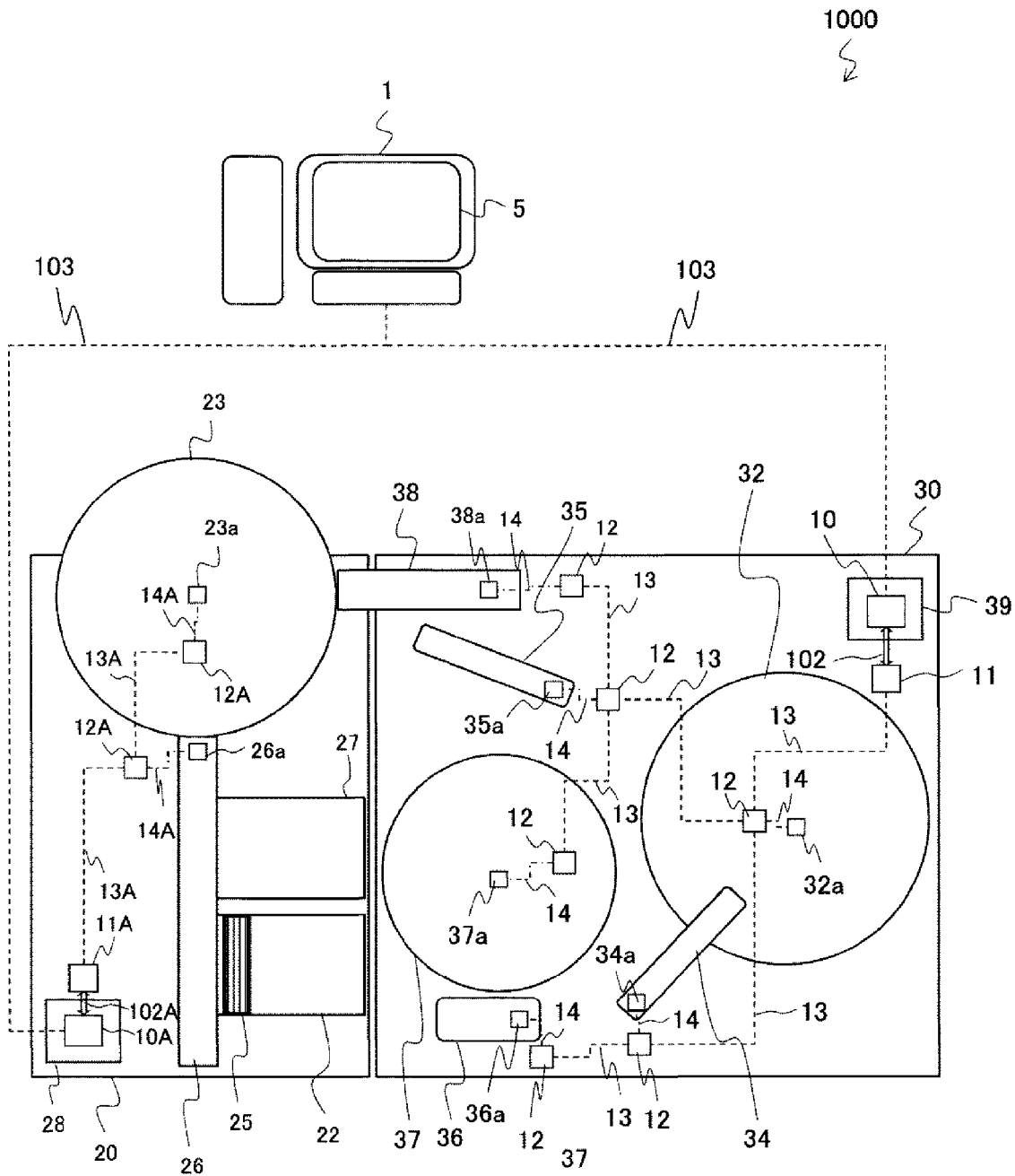

[FIG. 2]
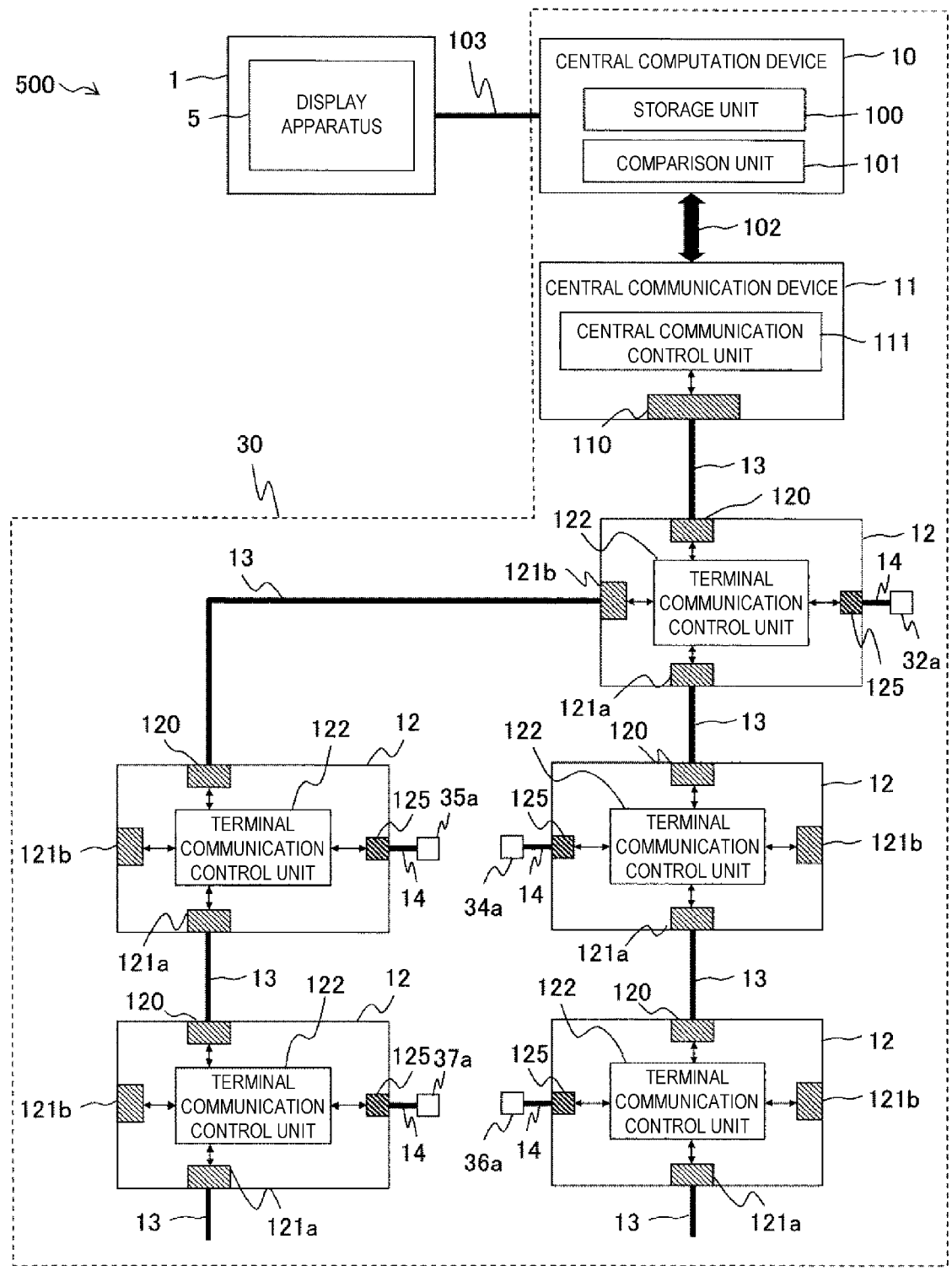

[FIG. 3]
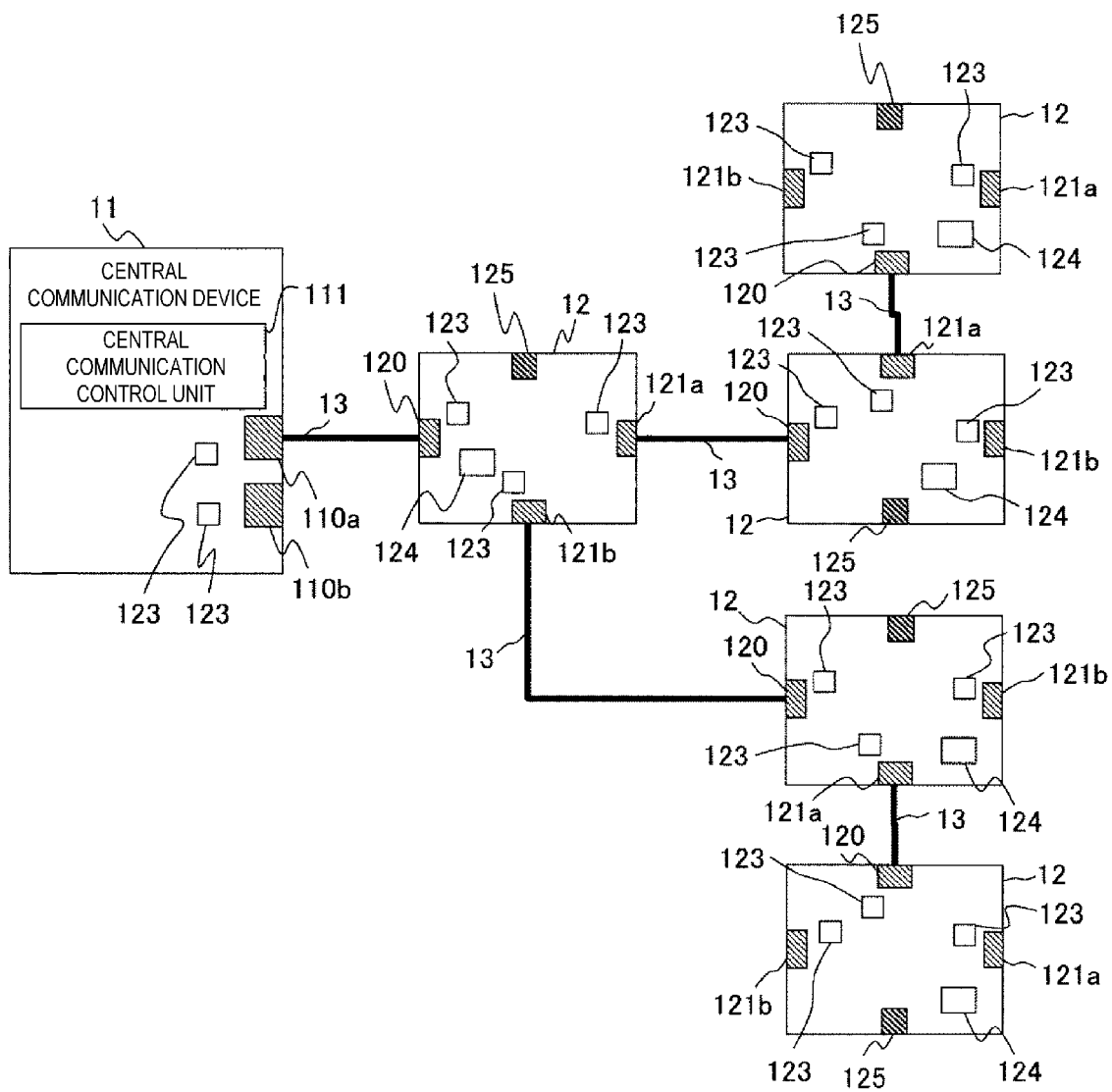

[FIG. 4]
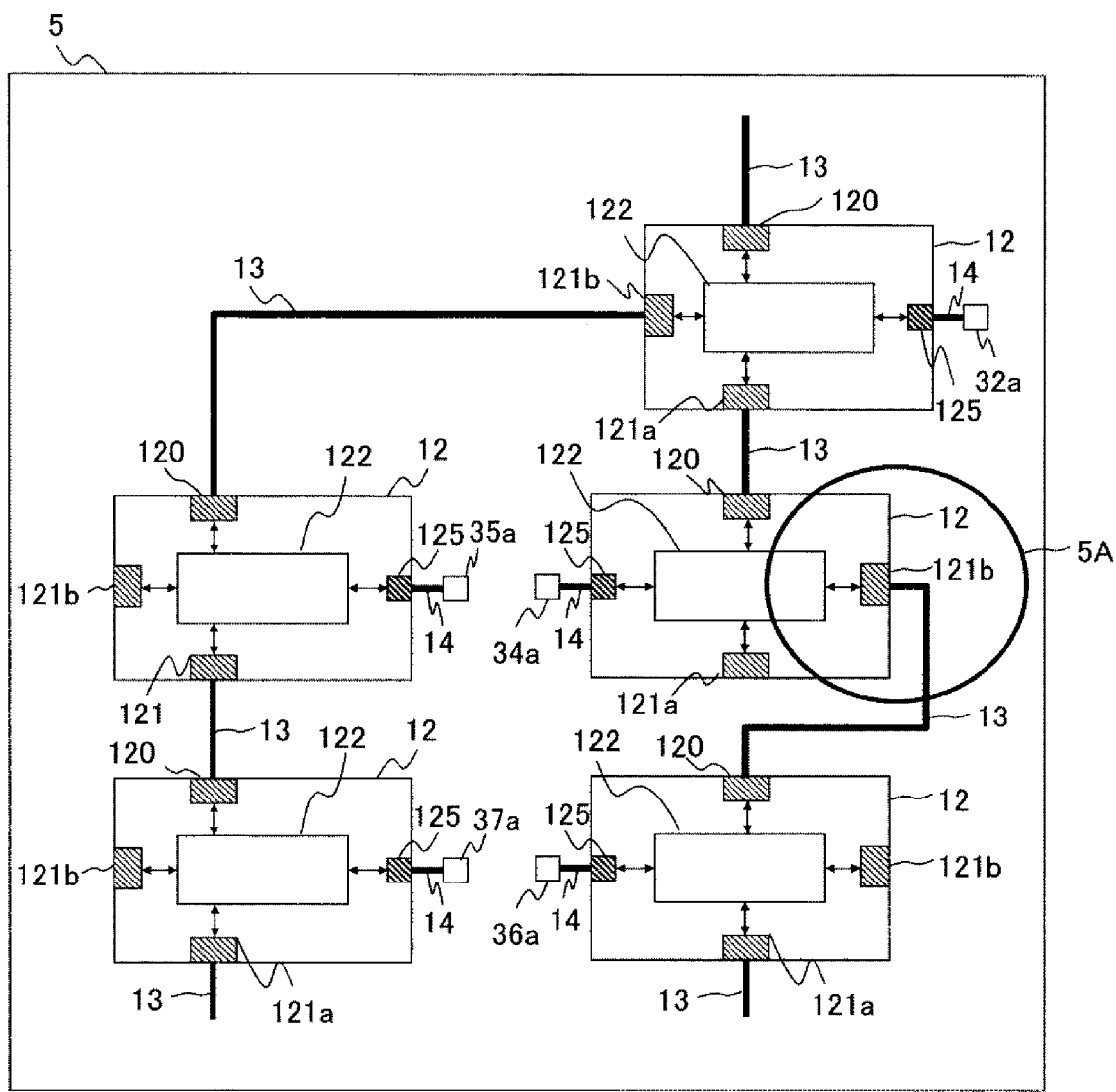

[FIG. 5]
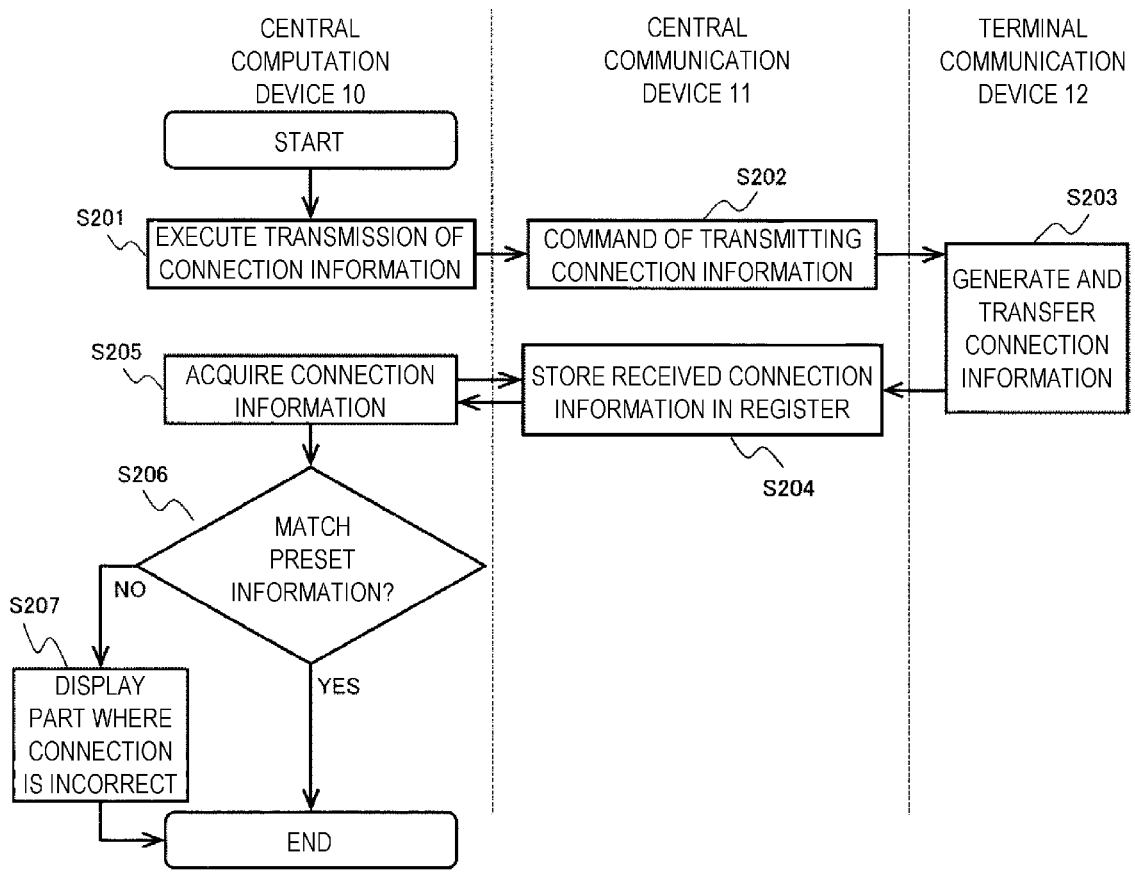
[FIG. 6]
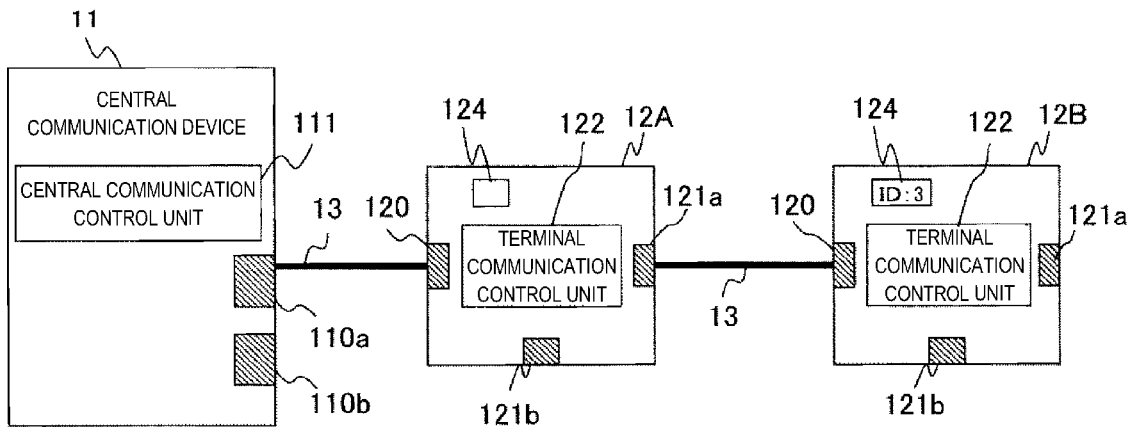

[FIG. 7]

| PORT NAME | NUMBER ADDED IN PORT NUMBER UNIT |
|---|---|
| TERMINAL COMMUNICATION DEVICE 12 ITSELF | 1 |
| DOWNSTREAM COMMUNICATION PORT 1 (110a, 121a) | 2 |
| DOWNSTREAM COMMUNICATION PORT 2 (110b, 121b) | 3 |

[FIG. 8]

| Tail | PORT NUMBER UNIT 2 | PORT NUMBER UNIT 1 | PORT NUMBER UNIT 0 | ID |
|---|---|---|---|---|
| 0x0 | 0 | 0 | 1 | 3 |

[FIG. 9]

| Tail | PORT NUMBER UNIT 2 | PORT NUMBER UNIT 1 | PORT NUMBER UNIT 0 | ID |
|---|---|---|---|---|
| 0x1 | 0 | 2 | 1 | 3 |

[FIG. 10]

| Tail | PORT NUMBER UNIT 2 | PORT NUMBER UNIT 1 | PORT NUMBER UNIT 0 | ID |
|---|---|---|---|---|
| 0x2 | 2 | 2 | 1 | 3 |

[FIG. 11]

| CONNECTION STATE | LIGHTING STATE |
|---|---|
| NORMAL | ON |
| COMMUNICATION ERROR | BLINK |
| DISCONNECTION | OFF |

DISTRIBUTED CONTROL SYSTEM, AUTOMATIC ANALYSIS DEVICE, AND AUTOMATIC ANALYSIS SYSTEM

TECHNICAL FIELD

The present invention relates to a distributed control system, an automatic analysis device, and an automatic analysis system.

BACKGROUND ART

For the purpose of immediately finding an error in amounting position of each device connected to a processing device and improving the efficiency of connection work, PTL 1 describes a device that includes a configuration instruction information table that retains information related to a connection instruction of a device based on a configuration instruction sheet, a configuration confirmation information table that retains information related to a connection state of an actually connected device, and a comparator that compares the configuration instruction information table with the configuration confirmation information table, in which an error is displayed on a display device and a corresponding LED blinks when the comparator detects a mismatch.

CITATION LIST

Patent Literature

PTL 1: JP-A-10-334035

SUMMARY OF INVENTION

Technical Problem

In an industrial system such as an automatic analysis device, a centralized control device that directly connects transmission lines of control devices such as drive shafts and sensors mounted on the control devices to each control device have been used for a long time.

In such an industrial system, in recent years, in order to reduce a size of a device and improve the efficiency of design, manufacturing, and maintenance, it is required to reduce wirings of electronic control systems.

Further, in order to improve cost competitiveness and device reliability, in recent years, there is a demand for a technique that guarantees device control performance while minimizing an analog transmission line length by modularizing and distributedly arranging the control boards.

However, when a plurality of control boards are distributedly arranged in the same device, there is a problem that a communication error such as an erroneous connection or breakage, or a defect such as a disconnection is more likely occurs. Therefore, there is a long-awaited technique of immediately finding an erroneous connection or the like so as to improve the efficiency of the connection work.

As an example of the technique for solving these problems, a method of detecting a match or a mismatch between two pieces of information by comparing connection information of an actually connected device with information retaining a correct connection state of a device can be considered. As such a technique, for example, there is a technique described in the above-described PTL 1.

However, in PTL 1, it is assumed only a case that a connection device is connected to an information processing device in a situation where an erroneous connection is detected. For this reason, there is a problem that when the connection device is further branched from the connection device to another connection device, it is not possible to identify an abnormal part because no consideration is given to detecting which connection device or communication cable is erroneously connected or is failing.

In particular, in an automatic analysis device that performs qualitative and quantitative analysis of biological samples such as blood and urine, in response to a demand to integrate testing operations, there is an increasing need for an automatic analysis device in which analysis units using different measurement methods such as biochemical items and immune items are connected to one independent transport unit and the analysis units can be flexibly changed according to an operation of a user. In this background, in recent years, the number of modular type devices in which the transport unit and the analysis unit are implemented by independent computers has been increasing.

Further, in response to a demand for space saving, there is an increasing need for an automatic analysis device in which analysis units using different measurement methods such as the above-described electrolyte items and biochemical items are integrated into one analysis unit.

These needs are required not only for large-sized and medium-sized automatic analysis devices that process a large number of samples per day, but also for small-sized automatic analysis devices.

In order to satisfy the demands of such an automatic analysis device, it is desired to apply a distributed control system in which control boards are modularized and distributedly arranged. Therefore, there are expectations for a technique for quickly finding erroneous connections and defects in the automatic analysis device so as to improve the efficiency of the connection work.

The invention provides a distributed control system and an automatic analysis device provided with the same, and an automatic analysis system, whereby erroneous connections or defects can be more easily and reliably detected than in the related art, even when a plurality of control boards are distributedly arranged in the same device.

Solution to Problem

The invention includes a plurality of devices that solve the above problems, and an example thereof is provided. A distributed control system, includes: a central computation device; a central communication device configured to manage communication control; a plurality of terminal communication devices to which at least one control object device is connected; a communication path connecting the central communication device and the terminal communication device; and a display device, in which the central computation device includes a storage unit retaining correct connection information, and a comparison unit configured to compare the correct connection information with connection information of an actually connected control object device or terminal communication device, the central communication device includes a central communication control unit configured to control communication of the distributed control system, and a plurality of communication ports, the terminal communication device includes a terminal communication control unit configured to execute communication control, at least one upstream communication port, at least one downstream communication port, and an individual identifiable ID setting unit, the central computation device is configured to output, when determination that an error has occurred is made as a result of comparison of the correct connection information retained in the storage unit and the connection information of the actually connected control object device or terminal communication device by the comparison unit, a display signal of an abnormal part to the display device, and the display device is configured to display the abnormal part on the basis of the display signal.

Advantageous Effect

According to the invention, erroneous connections or defects can be more easily and reliably detected than in the related art, even when a plurality of control boards are distributedly arranged in the same device. Problems, configurations, and effects other than those described above will be further clarified with the following description of embodiments.

BRIEF DESCRIPTION OF DRAWINGS

FIG. 1 is a diagram showing an outline of an automatic analysis system provided with an automatic analysis device to which a distributed control system according to the invention is applied.

FIG. 2 is a diagram showing a configuration example of the distributed control system according to the invention.

FIG. 3 is a diagram showing a specific configuration example on a terminal communication device side in FIG. 2.

FIG. 4 is a diagram showing an example of a screen for displaying an abnormal part displayed on a display apparatus in the distributed control system according to the invention.

FIG. 5 is a flowchart showing a flow of an abnormality detection method in the distributed control system according to the invention.

FIG. 6 is a diagram showing an example of a method of adding data in the distributed control system according to the invention.

FIG. 7 is a diagram showing an example of a determination method of a port number by a port name in the distributed control system according to the invention.

FIG. 8 is a diagram showing an example of added data in the distributed control system according to the invention.

FIG. 9 is a diagram showing an example of added data in the distributed control system according to the invention.

FIG. 10 is a diagram showing an example of added data in the distributed control system according to the invention.

FIG. 11 is a diagram showing an LED display example of the terminal communication device in the distributed control system according to the invention.

DESCRIPTION OF EMBODIMENTS

Embodiments of a distributed control system, an automatic analysis device, and an automatic analysis system of the invention will be described with reference to FIGS. 1 to 11.

First, an overall configuration of the automatic analysis device or the automatic analysis system provided with the distributed control system of the present embodiment will be described with reference to FIG. 1. FIG. 1 is a diagram schematically showing the overall configuration of the automatic analysis device or the automatic analysis system including the distributed control system according to the present embodiment.

An automatic analysis system 1000 in FIG. 1 is a device for performing qualitative and quantitative analysis of a biological sample such as blood or urine (hereinafter referred to as a specimen), and mainly includes a transport unit 20, an analysis unit 30, and a control device 1.

The transport unit 20 is a unit for putting or collecting a specimen rack 25 equipped with one or more specimen containers containing the specimen into or from the automatic analysis system 1000, and at the same time, transporting the specimen rack 25 to the analysis unit 30.

The transport unit 20 includes a rack buffer 23, a rack supply tray 22, a rack storage tray 27, a transport line 26, a transport control unit 28, or the like.

In the transport unit 20, the specimen rack 25 disposed on the rack supply tray 22 is transported to the rack buffer 23 by the transport line 26. There is a specimen presence or absence determination sensor (not shown) in the middle of the transport line 26, and the presence or absence of the specimen container on the specimen rack 25 is recognized. Here, if it is determined that there is a specimen container, a specimen barcode (not shown) affixed on the specimen container is read by a specimen barcode reader (not shown) to recognize identification information of the specimen. In a real system, the identification information identifies a patient.

The rack buffer 23 has a rotor structure that performs circular motion, and has slots for radiatively retaining a plurality of specimen racks 25 on a concentric circle on which a plurality of specimen containers are placed on an outer circumference. By rotating the slots with a motor, the slots are configured to carry in and out any specimen rack 25 to a requested destination. According to such a structure, it is not always necessary to process the specimen racks 25 placed first in order. In other words, if a specimen rack has a high priority, the specimen rack can be processed first.

The transport line 26 is connected to a certain point on the radial circumference of the rack buffer 23, and the specimen rack 25 is carried in and out. If the point is at a position of 0 degrees on the circumference, a specimen dispensing line 38 for drawing the specimen rack 25 into the analysis unit 30 described later is connected to a position of 90 degrees on the circumference from the position where the transport line 26 is connected, and the specimen rack 25 is carried in and out.

The specimen rack 25 that has been dispensed in the analysis unit 30 waits for output of a measurement result, and if necessary, processing such as automatic retesting can be performed in the rack buffer 23. Further, when the processing is completed, the specimen rack 25 is transported to the rack storage tray 27 via the transport line 26.

The transport control unit 28 is a unit that executes control of an operation of transporting an appropriate specimen rack 25 from the rack buffer 23 to the specimen dispensing line 38 and an operation of returning the specimen rack 25 from the specimen dispensing line 38 to the rack buffer 23. The transport control unit 28 controls a transport operation for transporting the specimen to the analysis unit 30. Therefore, the transport control unit 28 is connected to a motor 23a for rotationally driving the rack buffer 23 or a motor 26a for driving the transport line 26 by a distributed control system 500 (see FIG. 2).

The control device 1 includes user interfaces such as a display apparatus 5 that displays an operation screen for ordering a measurement item to be measured for a specimen to be measured and an operation screen for confirming a measurement result, and an input device that inputs various instructions. The control device 1 is a unit that plays a role of managing information of units of the entire automatic analysis system 1000. The control device 1 is connected to the analysis unit 30 and the transport unit 20 via a wired or wireless network line 103.

The analysis unit 30 is a unit that performs a measurement operation for the measurement item requested for the specimen and outputs the measurement result, and is connected to the transport unit 20. The analysis unit 30 includes a reaction disk 37, a reagent disk 32, a reagent probe 34, a sample probe 35, the specimen dispensing line 38, a biochemical measurement unit 36, and a control unit 39.

Reaction containers (not shown) are arranged on a circumference of the reaction disk 37. The specimen dispensing line 38 for carrying in the specimen rack 25 on which the specimen container is placed is disposed near the reaction disk 37. A motor 37a for rotating the reaction disk 37 is connected to the reaction disk 37.

The specimen dispensing line 38 is a line for transporting the specimen rack 25 transported from the rack buffer 23 to a dispensing position and returning the specimen rack 25 after dispensing to the rack buffer 23, and is driven by a motor 38a.

The sample probe 35 that can rotate and move up and down is disposed between the reaction disk 37 and the specimen dispensing line 38. The sample probe 35 moves while drawing an arc around a rotation axis to dispense the specimen from the specimen rack 25 to the reaction container. A motor 35a and a syringe (not shown) for rotating and moving the sample probe 35 up and down are connected to the sample probe 35.

The reagent disk 32 is a storage in which a plurality of reagent bottles (not shown) containing a reagent can be placed on the circumference. The reagent disk 32 is kept cold. A motor 32a for rotating the reagent disk 32 is connected to the reagent disk 32.

The reagent probe 34 that can rotate and move up and down is disposed between the reaction disk 37 and the reagent disk 32. The reagent probe 34 moves while drawing an arc around a rotation axis, accesses the inside of the reagent disk 32 from a reagent probe aspiration port, and dispenses the reagent from the reagent bottles to the reaction containers. A motor 34a and a syringe (not shown) for rotating and moving the reagent probe 34 up and down are connected to the reagent probe 34.

Further, washing tanks (not shown) are disposed within operation ranges of the reagent probe 34 and the sample probe 35, respectively.

The biochemical measurement unit 36 is further arranged around the reaction disk 37.

The biochemical measurement unit 36 is an analysis unit that analyzes biochemical components in the specimen by measuring an absorbance of a reaction solution produced by mixing and reacting in the reaction containers on the reaction disk 37. The biochemical measurement unit 36 includes a light source, a spectrophotometer 36a, or the like.

The control unit 39 arranged in the analysis unit 30 is connected to each mechanism in the analysis unit 30 described above by the distributed control system 500 (see FIG. 2), and controls an operation of the mechanism. FIGS. 1 and 2 show a case where the motors 32a, 34a, 35a, 37a, and 38a, as well as the spectrophotometer 36a in the analysis unit 30 are connected to the control unit 39. In FIG. 2, for convenience of illustration, a line connected to the motor 38a is omitted.

The above is the overall outline configuration of the automatic analysis system 1000 according to the present embodiment.

Although FIG. 1 describes a system including the transport unit 20, the analysis unit 30, and the control device 1, the automatic analysis system 1000 shown in FIG. 1 is only an example. For example, an analysis unit that executes measurement of a different measurement item (for example, an immunological item) may be connected to the automatic analysis system 1000 shown in FIG. 1, an analysis unit that has the same configuration as that of the analysis unit 30 may be further connected to the automatic analysis system 1000, and an analysis unit for measuring a different analysis item (for example, an electrolyte item) may be further arranged in the analysis unit 30.

Further, the distributed control system 500 of the invention can also be applied to an automatic analysis device formed by only the analysis unit 30 with the transport unit 20 being omitted. Furthermore, the distributed control system. 500 can also be applied to each device in an automatic analysis system formed by an automatic analysis device and a specimen pretreatment device that performs various pretreatments such as centrifugation and subdivision dispensing of a specimen before measurement.

Next, an outline of a mechanical operation of the automatic analysis system 1000 shown in FIG. 1 will be described.

The transport unit 20 sends the specimen racks 25 disposed on the rack supply tray 22 of the automatic analysis system 1000 one by one onto the transport line 26, and carries the specimen racks 25 into the rack buffer 23. The specimen racks 25 transported to the rack buffer 23 are transported to the specimen dispensing line 38 of the analysis unit 30.

When the specimen rack 25 arrives at the specimen dispensing line 38 of the analysis unit 30, on each specimen mounted on the specimen rack 25, a dispensing operation is performed by the sample probe 35 according to the measurement item requested by the control device 1. The sample probe 35 discharges the aspirated specimen into the reaction container on the reaction disk 37, and the reagent aspirated from the reagent disk 32 by the reagent probe 34 is further added to the reaction container and the mixture is stirred. Thereafter, the absorbance is measured by the biochemical measurement unit 36, and a measurement result is transmitted to the control device 1.

The control device 1 acquires a concentration of a specific component in the specimen by arithmetic processing on the basis of the transmitted measurement result, displays the concentration on the display apparatus 5, and stores the concentration in a storage unit (not shown).

Next, a specific configuration of the distributed control system according to the present embodiment will be described with reference to FIGS. 2 to 4. FIG. 2 is a diagram showing a configuration example of the distributed control system 500 according to present embodiment. FIG. 3 is a diagram showing a specific configuration example on a terminal communication device 12 side in FIG. 2. FIG. 4 is a diagram showing an example of a screen for displaying an abnormal part displayed on the display apparatus 5.

As shown in FIG. 2, the distributed control system 500 includes the display apparatus 5, a central computation device 10, a central communication device 11, a plurality of terminal communication devices 12, a network communication path 13, and a communication path 14.

The central computation device 10 is connected to the central communication device 11 via a data transmission unit 102, and is also connected to the control device 1 including the display apparatus 5 via a network line 103.

As shown in FIG. 2, the central computation device 10 includes a storage unit 100 retaining correct connection information, and a comparison unit 101 comparing the correct connection information retained in the storage unit 100 with connection information of an actually connected device (control object device or terminal communication device 12).

The central computation device 10 outputs, when determination that an abnormality has occurred is made as a result of comparison of the correct connection information retained in the storage unit 100 and the connection information of the actually connected control object device or terminal communication device 12 by the comparison unit 101, an identification display signal for identifying an abnormal part to the display device.

The connection information used in the central computation device 10 includes port number identification information for identifying communication ports 110, 120, and 121, which will be described later, and individual identification information set by an ID setting unit 124, which will be described later. These details will be described later with reference to FIG. 7 and following figures.

The data transmission unit 102 that connects the central computation device 10 and the central communication device 11 and the network line 103 that connects the central computation device 10 and the control device 1 consist of bus forms such as peripheral component interconnect (PCI: registered trademark) and versa module eurocard (VME: registered trademark), and data transmission paths that are serial communication such as universal serial bus (USB) and serial peripheral interface (SPI).

The central communication device 11 is connected to the plurality of terminal communication devices 12 by the network communication path 13, and executes integrated management of communication control as a master station of communication in the distributed control system 500.

As shown in FIGS. 2 and 3, the central communication device 11 includes a central communication control unit 111 that controls the communication of the distributed control system 500, and the communication port 110. The central communication device 11 controls the terminal communication device 12 via the communication port 110.

As shown in FIG. 3, a plurality of communication ports 110 (communication ports 110a, 110b, . . . ) are provided, but for convenience of description, the communication ports 110 will be described as one.

As shown in FIGS. 2 and 3, the terminal communication device 12 is connected to the central communication device 11 or another terminal communication device 12 by the network communication path 13, and communicates with the central communication device 11 or another terminal communication device 12. In particular, the terminal communication device 12 generates its own connection information. Further, the terminal communication device 12 transmits the connection information on a downstream side to the central computation device 10 on an upstream side.

Further, as shown in FIG. 2, each terminal communication device 12 is connected to, via the communication path 14, the corresponding motors 32a, 34a, 35a, and 37a, as well as the spectrophotometer 36a which are serving as the control object devices in the analysis unit 30.

As shown in FIGS. 2 and 3, the terminal communication device 12 includes an upstream communication port 120, two downstream communication ports 121a, 121b, a terminal communication control unit 122 that executes communication control, light emitting diodes (LEDs) 123 that indicate a communication state with the central communication device 11 or the terminal communication device 12 connected upstream or downstream, the individual identifiable ID setting unit 124, and a communication port 125 for connecting to the control object devices.

The upstream communication port 120 is connected to the communication port 110 of the central communication device 11 or the downstream communication ports 121a, 121b of another terminal communication device 12. The downstream communication ports 121a, 121b are connected to the upstream communication port 120 of another terminal communication device 12.

The LEDs 123 indicating the communication state are mounted on the upstream communication port 120 and the downstream communication ports 121a, 121b of the terminal communication device 12, respectively, and are provided in the same number as the upstream communication port 120 and the downstream communication ports 121a, 121b. The LED 123 functions as a display device indicating the communication state with the central communication device 11 or the terminal communication device 12 connected upstream or downstream.

The ID setting unit 124 is a unit for setting individual identification information of each terminal communication device 12, and is set in one distributed control system 500 without overlapping each other. As a device for setting the ID, for example, a read-only memory (ROM), a switch, or the like is assumed.

The display device in the present embodiment includes the LED 123 provided in the terminal communication device 12 and indicating the communication state with the central communication device 11 or the terminal communication device 12, and the display apparatus 5 connected to the central computation device 10.

The display device displays an abnormal part on the basis of the identification display signal of the abnormal part generated by the comparison unit 101 of the central computation device 10. For example, when there is an abnormal part, it is possible to identify a content of the abnormality by a lighting mode of the LED 123. Further, as shown in FIG. 4, an abnormal part 5A can be identified by highlighting the abnormal part 5A on the display apparatus 5.

Next, an acquisition method of connection information in the distributed control system 500 according to the present embodiment will be described with reference to FIGS. 5 to 11. FIG. 5 is a flowchart of a procedure for acquiring an actual connection state of the terminal communication device 12 in the distributed control system 500. FIG. 6 is a diagram showing an example of a method of adding data in the terminal communication device 12. FIG. 7 is a diagram showing an example of a determination method of a port number by a port name. FIGS. 8 to 10 are diagrams showing an example of added and generated connection information data. FIG. 11 is a diagram showing an LED display example of the terminal communication device.

A timing of acquiring the connection information in the distributed control system 500 described below is, for example, when checking wirings at the time of manufacturing the automatic analysis system 1000, the transport unit 20, and the analysis unit 30, and when confirming startup after replacing a board during maintenance of the automatic analysis system 1000, the transport unit 20, and the analysis unit 30.

As a general overview, in the distributed control system 500 of the present embodiment, connection information, which includes the port number identification information for identifying a path of the terminal communication device 12 through which the terminal communication device 12 is retained and information of an individual identifiable ID, is acquired via the network communication path 13 between the terminal communication device 12 and the central communication device 11 or between a terminal communication device 12 and a terminal communication device 12.

The flowchart in FIG. 5 shows the procedure for acquiring the connection information retained by the terminal communication device 12 from the central computation device 10 via the data transmission unit 102, the central communication device 11, and the network communication path 13 in the distributed control system 500.

The correct connection information to be compared with in the central computation device 10 is preset and stored in the storage unit 100.

First, the central computation device 10 outputs a command for acquiring connection information to the central communication device 11 (step S201).

Next, on the basis of the command from the central computation device 10, the central communication device 11 transfers data to the terminal communication device 12 by accessing an operation register (step S202). At this time, all register regions related to the connection information are cleared to 0.

Next, the terminal communication device 12 that receives the command from the central communication device 11 generates its own connection information and transfers the data to the central communication device 11 (step S203). Further, the transfer is executed while adding the data of the terminal communication device 12 relayed in a path connected from the terminal communication device 12 to another terminal communication device 12.

Next, the central communication device 11 stores the connection information in a register after receiving the transfer from the terminal communication device 12 (step S204). Therefore, the central computation device 10 reads and acquires the information received by the central communication device 11 and stored in the register in step S204 (step S205).

Next, in the central computation device 10, the correct connection information retained by the storage unit 100 and the actually acquired connection information are compared in the comparison unit 101 of the central computation device 10 (step S206). If the two pieces of connection information match in step S206, processing is completed. On the other hand, if the two pieces of connection information do not match, the processing proceeds to step S207, all parts where the connection is incorrect are output as an alarm to the display apparatus 5, the LEDs 123 corresponding to the abnormal parts are turned on, and the processing is completed.

Next, a method of generating and adding the connection information of the relayed terminal communication device 12 in step S203 in the flowchart shown in FIG. 5 will be described by taking a configuration shown in FIG. 6 as an example.

As shown in FIG. 6, in a method of generating and adding data according to the present embodiment, an example is shown in which a terminal communication device 12B whose individual identification ID is set to "3" is connected to the central communication device 11 via another terminal communication device 12A.

First, the terminal communication device 12B on the most downstream side stores its own ID "3" in an ID unit of the connection information data to be transferred.

Further, the terminal communication device 12B stores a port number "1" in a port number unit 0 of the connection information data. The port number unit is a number for identifying a port for outputting connection information when the device is in a position of generating connection information, and a port for receiving connection information when the device is in a position of mediating the connection information. For example, the numbers shown in FIG. 7 are assigned, when the port name is "terminal communication device 12 itself", the number added in the port number unit is "1", when the port name is "downstream communication port 1 (110a, 121a)", the number added in the port number unit is "2", and when the port name is "downstream communication port 2 (110b, 121b)", the number added in the port number unit is "3". The port number corresponds to the port number identification information. In this case, since the terminal communication device 12B generates connection information and outputs the connection information from the upstream communication port 120 to the upstream side, the port number thereof is stored as "1".

Further, the terminal communication device 12B stores "0" in a Tail unit indicating a storage slot of the port number in the connection information data.

As a result, the generated connection information data has a form as shown in FIG. 8.

Next, the terminal communication device 12A on the upstream side, which has received the connection information data as shown in FIG. 8 generated by the terminal communication device 12B on the most downstream side, calculates the next storage slot (reference value+1) by referring to the Tail unit for the connection information data, and updates the Tail unit.

Further, since the terminal communication device 12A itself receives the connection information data from the terminal communication device 12B at the downstream communication port 121a, the port number 2 of the downstream communication port 121a used in the terminal communication device 12A is stored into the port number unit 1, which is the storage slot of the port number unit.

The connection information data added in the terminal communication device 12A has a form shown in FIG. 9. The terminal communication device 12A outputs the connection information data to the central communication device 11.

Finally, the connection information data added in the terminal communication device 12A as shown in FIG. 9 is also added in the central communication device 11. The central communication device 11 also calculates the next storage slot (reference value+1) by referring to the Tail unit, and updates the Tail unit. Further, the port number "2" that identifies the communication port 110a through which data passes is stored in the port number unit 2, which is the storage slot of the port number unit.

That is, at the stage when the connection information data generated by the terminal communication device 12B whose individual identification ID is set to "3" is input to the central computation device 10, as shown in FIG. 10, the Tail unit is "0x2", the port number unit is "0x221", and the ID unit is "0x3". Therefore, it is possible to identify a mounting position of the terminal communication device 12B whose individual identification ID is set to 3. From the above, it is possible to acquire the connection information indicating which place of which path the terminal communication device 12 is in.

The central communication device 11 outputs the added connection information data as shown in FIG. 10 to the central computation device 10.

The central computation device 10 compares the received connection information with the correct connection information stored in the storage unit 100 in step S206 of the flowchart shown in FIG. 5, and determines whether an error such as a communication failure or a disconnection has occurred in the network communication path 13 between the central communication device 11 and the terminal communication device 12A on the most downstream side.

If the connection information has different parts, the central computation device 10 identifies, by referring to each storage slot of the connection information data, the terminal communication device 12 or a cable of the network communication path 13 which causes the communication failure or the disconnection in the network communication path 13.

For example, when the numbers in the port number units are different, it means that an erroneous connection has occurred in which a connected port or the connection order is erroneous. Further, it is possible to identify a position where the erroneous connection occurs based on a position of the different port numbers.

Further, when the number of the port number units is different or there is no response, it means that breakage or disconnection has occurred. In this case, it is also possible to identify a part where the breakage or the disconnection has occurred on the basis of the number of the port number units or the absent port number unit.

Further, the identified part is visualized, an error signal is output from the central computation device 10 to the display apparatus 5, and the error and the abnormal part as shown in FIG. 4 are displayed.

It is desirable that the error notification is executed when a response of data from the terminal communication device 12 to the central communication device 11 cannot be confirmed within a timeout time determined by the central computation device 10. In this case, the central communication device 11 can only detect a path where an error has occurred. The path here is preferably determined by the communication ports 110a, 110b to which the terminal communication device 12 is connected among the plurality of communication ports 110a, 110b of the central communication device 11.

Furthermore, it is desirable that it is possible to identify, by confirming the LED 123 mounted on the terminal communication device 12, the terminal communication device 12 or a cable of the network communication path 13 which cause a communication failure part or a disconnection part in the network communication path 13.

As described above, the central computation device 10 outputs, on the basis of a comparison result of the connection information, a lighting signal according to the corresponding connection state to the LED 123 corresponding to each communication port 110, 121a, and 121b of the central communication device 11 and the terminal communication device 12.

FIG. 11 is a diagram showing an example of an LED lighting mode for identifying a communication failure part or a disconnection part in the network communication path 13, and also the content of the error by confirming the LED 123 mounted on the terminal communication device 12.

For example, as shown in FIG. 11, the lighting mode of the LED 123 is "ON" when the connection state is "normal", "blink" when the connection state is "communication error" due to breakage or an erroneous connection, and "OFF" when the connection state is "disconnection".

Specifically, when there is an disconnection part, the LED 123 of the communication port 110 on the downstream side of the central communication device 11 or the downstream communication ports 121a, 121b of the terminal communication device 12 which are on the upstream side of the cable is turned on, and the LED 123 of the upstream communication port 120 of the terminal communication device 12 and others on the downstream side of the cable is turned off. Accordingly, the occurrence of a "disconnection" and the disconnection part can be clearly found at a glance.

Further, when a communication error occurs due to an erroneous connection or breakage in communication ports of the central communication device 11 and the terminal communication device 12, only an LED 123 corresponding to the communication port in which the error has occurred blinks as a communication error.

Accordingly, it is also possible to identify whether the error is due to the cable of the network communication path 13 or the error is due to the central communication device 11 or the terminal communication device 12 itself.

Next, the effect of the present embodiment will be described.

The distributed control system 500 of the present embodiment described above includes the central computation device 10, the central communication device 11 managing communication control, the plurality of terminal communication devices 12 to which at least one control object device is connected, the network communication path 13 connecting the central communication device 11 and the terminal communication device 12, and the display device. The central computation device 10 includes the storage unit 100 retaining the correct connection information, and the comparison unit 101 comparing the correct connection information with connection information of an actually connected control object device or terminal communication device 12. The central communication device 11 includes the central communication control unit 111 controlling communication of the distributed control system 500, and the plurality of communication ports 110. The terminal communication device 12 includes the terminal communication control unit 122 executing communication control, at least one upstream communication port 120, at least one downstream communication port 121, and the individual identifiable ID setting unit 124. When the determination that an error has occurred is made as a result of comparison of the correct connection information retained in the storage unit 100 and the connection information of the actually connected control object device or terminal communication device 12 by the comparison unit 101, the central computation device 10 outputs a display signal of an abnormal part to the display device. The display device displays the abnormal part on the basis of the display signal.

According to the distributed control system 500 of the present embodiment, it is possible to immediately find an abnormality between the central communication device 11 and the terminal communication device 12, and between the terminal communication device 12 and the terminal communication device 12. Therefore, even if a plurality of control boards for controlling apparatuses to be controlled are distributedly arranged in the same device, it is possible to detect an abnormal part in a system connecting the control boards more easily and reliably than in the related art, and it is possible to quickly correct the connection.

Further, the central communication device 11 controls the terminal communication device 12 via the communication port 110, or the terminal communication device 12 transmits the connection information on the downstream side to the central computation device 10 on the upstream side via the network communication path 13, so that one central computation device 10 or one central communication device 11 is disposed in the distributed control system 500. Therefore, the inside of the system can be controlled efficiently, and the efficiency of distributed control can be improved.

Further, the central computation device 10 outputs a command for acquiring connection information to the central communication device 11; the central communication device 11 transfers the command to the terminal communication device 12 once receiving the command from the central communication device 11; the terminal communication device 12 generates connection information on the basis of the command, and transfers the generated connection information to the central communication device 11; the central communication device 11 transfers the connection information to the central computation device 10 once receiving the connection information from the terminal communication device 12; and the central computation device 10 compares the connection information received from the central communication device 11 with the correct connection information, and outputs the display signal to the display device in a case of a mismatch. Therefore, the abnormal part can be identified more accurately and easily.

Further, the display device is at least one of the LED 123 provided in the terminal communication device 12 and indicating the communication state with the central communication device 11 or the terminal communication device 12, and the display apparatus 5 connected to the central computation device 10. Therefore, by confirming the display apparatus 5 and the LED 123, systematic troubleshooting that can identify an abnormal part and the content of the abnormality is enabled, and connection work can be performed more efficiently.

Further, when there is an abnormal part, it is possible to identify a content of the abnormality by a lighting mode of the LED 123. Therefore, the content of the abnormality can be grasped together with the part where the abnormality has occurred, and more appropriate measures can be taken.

Further, the same number of LEDs 123 as the upstream communication port 120 and the downstream communication port 121 are provided. Therefore, it is possible to more easily grasp the part where the erroneous connection has occurred.

As described above, in an automatic analysis device or an automatic analysis system where control boards are also desirably modularized and distributedly arranged, the control unit 39 which controls an operation of apparatuses in the analysis unit 30 that analyzes a sample and the apparatuses are connected by the distributed control system 500 according to the present embodiment, and each apparatus in the transport unit 20 which transports the sample to the analysis unit 30 and the transport control unit 28 are connected by the distributed control system 500 according to the present embodiment. Therefore, it is possible to quickly find out an erroneous connection or a defect and improve the efficiency of the connection work. Accordingly, in the automatic analysis device or the automatic analysis system, the efficiency of the connection work also can be improved, and the system configuration can be flexibly changed according to the operation of the user and space can be saved.

OTHER EMBODIMENTS

The invention is not limited to the above embodiment, and various modifications and applications can be made thereto. For example, the above-described embodiment has been described in detail in order to make the invention easy to understand, and the invention is not necessarily limited to those which have all the configurations described.

For example, in the above-described embodiment, the automatic analysis device or automatic analysis system is described as an example of a device or system equipped with the distributed control system, but the device or system on which the distributed control system is applicable is not limited to this, and the distributed control system of the invention can be applied to various devices or systems that require a plurality of control boards to be provided in the device or system.

REFERENCE SIGN LIST

1: control device
5: display apparatus
5A: abnormal part
10: central computation device
11: central communication device
12, 12A, 12B: terminal communication device
13: network communication path
14: communication path
20: transport unit
23a, 26a: motor
28: transport control unit
30: analysis unit (automatic analysis device)
32a, 34a, 35a, 37a, 38a: motor
36: biochemical measurement unit
36a: spectrophotometer
39: control unit
100: storage unit
101: comparison unit
102: data transmission unit
103: network line
110, 110a, 110b: communication port
111: central communication control unit
120: upstream communication port
121, 121a, 121b: downstream communication port
122: terminal communication control unit
123: LED
124: ID setting unit
125: communication port
500: distributed control system
1000: automatic analysis system

The invention claimed is:
1. A distributed control system, comprising:
a central computation device;
a central communication device configured to manage communication control;
a plurality of terminal communication devices to which at least one control object device is connected;
a communication path connecting the central communication device and the terminal communication device; and
a display device including at least an LED provided in the terminal communication device and indicating a communication state with the central communication device or the terminal communication device, wherein
the central computation device includes a storage unit retaining correct connection information, and a comparison unit configured to compare the correct connection information with connection information of an actually connected control object device or terminal communication device,
the central communication device includes a central communication control unit configured to control communication of the distributed control system, and a plurality of communication ports,
the terminal communication device includes a terminal communication control unit configured to execute communication control, at least one upstream communica- tion port, at least one downstream communication port, and an individual identifiable ID setting unit, the central computation device is configured to output, when determination that an error has occurred is made as a result of comparison of the correct connection information retained in the storage unit and the connection information of the actually connected control object device or terminal communication device by the comparison unit, a display signal of an abnormal part to the display device, and the LED has the same number as that of the upstream communication port and the downstream communication port, and is configured to display the abnormal part on the basis of the display signal such that when the abnormal part is present, a content of the abnormality is identifiable by a lighting mode of the LED.

2. The distributed control system according to claim 1, wherein
the central communication device is configured to control the terminal communication device via the communication port.

3. The distributed control system according to claim 1, wherein
the terminal communication device is configured to transmit connection information on a downstream side to the central computation device on an upstream side via the communication path.

4. The distributed control system according to claim 1, wherein
the central computation device is configured to output a command for acquiring connection information to the central communication device, the central communication device is configured to transfer the command to the terminal communication device once receiving the command from the central computation device, the terminal communication device is configured to generate connection information on the basis of the command, and transfer the generated connection information to the central communication device, the central communication device is configured to transfer the connection information to the central computation device once receiving the connection information from the terminal communication device, and the central computation device is configured to compare the connection information received from the central communication device with the correct connection information, and output the display signal to the display device in a case of a mismatch.

5. The distributed control system according to claim 1, wherein
the display device further includes a display apparatus connected to the central computation device.

6. The distributed control system according to claim 1, wherein
the connection information includes port number identification information for identifying the communication port.

7. The distributed control system according to claim 1, wherein
the connection information includes individual identification information set by the ID setting unit.

8. An automatic analysis device that analyzes a sample, wherein
a control unit configured to control an operation of apparatuses in the automatic analysis device and the apparatuses are connected by the distributed control system according to claim 1.

9. An automatic analysis system that analyzes a sample, comprising:
an analysis unit configured to measure the sample;
a transport unit configured to transport the sample to the analysis unit;
an analysis unit control unit configured to control an operation of each apparatus in the analysis unit; and
a transport unit control unit configured to control an operation of each apparatus in the transport unit, wherein
each apparatus in the analysis unit and the analysis unit control unit are connected by the distributed control system according to claim 1, and
each apparatus in the transport unit and the transport unit control unit are connected by the distributed control system according to claim 1.

* * * * *